(12) United States Patent
Bunza et al.

(10) Patent No.: US 7,812,731 B2
(45) Date of Patent: Oct. 12, 2010

(54) SENSORS AND SYSTEMS FOR DETECTING ENVIRONMENTAL CONDITIONS OR CHANGES

(75) Inventors: Geoffrey J. Bunza, Beaverton, OR (US); Steven W. Hudnut, Beaverton, OR (US)

(73) Assignee: Vigilan, Incorporated, Wilsonville, OR (US)

( * ) Notice: Subject to any disclaimer, the term of this patent is extended or adjusted under 35 U.S.C. 154(b) by 632 days.

(21) Appl. No.: 11/615,313

(22) Filed: Dec. 22, 2006

(65) Prior Publication Data

US 2008/0150732 A1      Jun. 26, 2008

(51) Int. Cl.
    *G08B 23/00* (2006.01)

(52) U.S. Cl. ............... 340/573.5; 340/573.1; 340/540; 340/572.1

(58) Field of Classification Search ............... 340/573.5, 340/572.1
    See application file for complete search history.

(56) References Cited

U.S. PATENT DOCUMENTS

| | | | |
|---|---|---|---|
| 4,137,361 A | 1/1979 | Deffeyes et al. | |
| 4,161,564 A | 7/1979 | Legbandt | |
| 4,218,507 A | 8/1980 | Deffeyes et al. | |
| 4,448,637 A | 5/1984 | Hiraishi et al. | |
| 4,545,914 A | 10/1985 | Graiver et al. | |
| 4,547,312 A | 10/1985 | Graiver et al. | |
| 5,018,180 A | 5/1991 | Shoulders | |
| 5,054,047 A | 10/1991 | Shoulders | |
| 5,123,039 A | 6/1992 | Shoulders | |
| 5,148,461 A | 9/1992 | Shoulders | |
| 5,188,890 A | 2/1993 | Ohashi et al. | |
| 5,190,813 A | 3/1993 | Ohashi et al. | |
| 5,236,512 A | 8/1993 | Rogers et al. | |
| 5,298,058 A | 3/1994 | Matsui et al. | |
| 5,336,869 A | 8/1994 | Kumar | |
| 5,356,579 A | 10/1994 | Jennings et al. | |

(Continued)

FOREIGN PATENT DOCUMENTS

DE      4444264 C1      4/1996

(Continued)

OTHER PUBLICATIONS

Finkenzeller, Klaus, *RFID Handbook: Fundamentals and Applications in Contactless Smart Cards and Identification*, John Wiley & Sons Ltd., England. (2003) pp. 1-9, 22-23, 26-27, 29-59, 106-112, 117-119.

(Continued)

*Primary Examiner*—Toan N Pham
*Assistant Examiner*—Kerri McNally
(74) *Attorney, Agent, or Firm*—Schwabe, Williamson & Wyatt

(57) ABSTRACT

Sensors and systems for detecting predetermined environmental conditions or changes may include a device capable of storing, representing, or providing information, and a shield. The shield may be disposed proximate the device. The shield may have a first condition and a second condition. In the first condition the shield is configured to prevent access to information stored in or on, represented by or provided by the device. In the second condition the shield is configured to permit access to information stored in or on, represented by or provided by the device. The shield may be configured to transition from the first condition to the second condition when the shield is exposed to the predetermined environmental condition.

33 Claims, 3 Drawing Sheets

U.S. PATENT DOCUMENTS

| | | | |
|---|---|---|---|
| 5,358,676 A | 10/1994 | Jennings et al. | |
| 5,399,413 A | 3/1995 | Katsen et al. | |
| 5,462,771 A | 10/1995 | Motoki et al. | |
| 5,525,423 A | 6/1996 | Liberman et al. | |
| 5,527,850 A | 6/1996 | Katayama et al. | |
| 5,549,851 A | 8/1996 | Fukushima et al. | |
| 5,557,263 A | 9/1996 | Fisher et al. | |
| 5,557,279 A | 9/1996 | D'hont | |
| 5,570,082 A | 10/1996 | Mahgerefteh et al. | |
| 5,573,610 A | 11/1996 | Koch et al. | |
| 5,573,611 A | 11/1996 | Koch et al. | |
| 5,635,292 A | 6/1997 | Jennings et al. | |
| 5,637,412 A | 6/1997 | Jennings et al. | |
| 5,781,110 A | 7/1998 | Habeger, Jr. et al. | |
| 5,858,600 A | 1/1999 | Itakura et al. | |
| 5,876,586 A | 3/1999 | Fukushima et al. | |
| 5,904,671 A | 5/1999 | Navot et al. | |
| 5,909,171 A | 6/1999 | Kyrtsos | |
| 5,910,766 A | 6/1999 | Evans | |
| 5,955,192 A | 9/1999 | Fukushima et al. | |
| 5,992,739 A | 11/1999 | Maeder | |
| 6,091,607 A | 7/2000 | McKeown et al. | |
| 6,097,297 A * | 8/2000 | Fard | 340/604 |
| 6,110,651 A | 8/2000 | Fukushima et al. | |
| 6,147,662 A | 11/2000 | Grabau et al. | |
| 6,154,137 A | 11/2000 | Goff et al. | |
| 6,294,997 B1 | 9/2001 | Paratore et al. | |
| 6,344,155 B1 | 2/2002 | Kitahara et al. | |
| 6,344,309 B2 | 2/2002 | Fukushima et al. | |
| 6,346,886 B1 | 2/2002 | De La Huerga | |
| 6,356,201 B1 | 3/2002 | Alles | |
| 6,373,395 B1 | 4/2002 | Kimsey | |
| 6,455,770 B2 | 9/2002 | Pulver | |
| 6,463,798 B2 | 10/2002 | Niekerk et al. | |
| 6,501,375 B1 | 12/2002 | Weant et al. | |
| 6,506,872 B2 | 1/2003 | Kimura et al. | |
| 6,541,346 B2 | 4/2003 | Malik | |
| 6,582,767 B1 | 6/2003 | Fukushima et al. | |
| 6,583,722 B2 | 6/2003 | Jeutter et al. | |
| 6,586,931 B2 | 7/2003 | Taicher | |
| 6,603,403 B2 * | 8/2003 | Jeutter et al. | 340/604 |
| 6,606,247 B2 | 8/2003 | Credelle et al. | |
| 6,607,825 B1 | 8/2003 | Wang et al. | |
| 6,639,304 B1 | 10/2003 | Oggioni et al. | |
| 6,673,999 B1 | 1/2004 | Wang et al. | |
| 6,696,937 B1 | 2/2004 | Keifer | |
| 6,713,327 B2 | 3/2004 | Leedy | |
| 6,713,671 B1 | 3/2004 | Wang et al. | |
| 6,753,771 B2 | 6/2004 | Lesesky | |
| 6,765,144 B1 | 7/2004 | Wang et al. | |
| 6,774,800 B2 | 8/2004 | Friedman et al. | |
| 6,806,122 B2 | 10/2004 | Oggioni et al. | |
| 6,846,985 B2 | 1/2005 | Wang et al. | |
| 6,846,994 B2 | 1/2005 | Wenner | |
| 6,864,418 B2 | 3/2005 | Wang et al. | |
| 6,891,110 B1 | 5/2005 | Pennaz et al. | |
| 6,894,145 B2 | 5/2005 | Xiao et al. | |
| 6,894,362 B2 | 5/2005 | Malik | |
| 6,898,489 B1 | 5/2005 | Hayes, Sr. | |
| 6,903,850 B2 | 6/2005 | Kay et al. | |
| 6,916,968 B2 | 7/2005 | Shapira et al. | |
| 6,933,848 B1 | 8/2005 | Stewart et al. | |
| 6,940,408 B2 | 9/2005 | Ferguson et al. | |
| 6,940,455 B2 | 9/2005 | Plettner | |
| 6,956,283 B1 | 10/2005 | Peterson | |
| 6,959,986 B2 | 11/2005 | Ushirogouchi et al. | |
| 6,970,092 B2 * | 11/2005 | Hum et al. | 340/573.4 |
| 6,980,865 B1 | 12/2005 | Wang et al. | |
| 7,022,388 B2 | 4/2006 | Hashimoto et al. | |
| 7,053,781 B1 | 5/2006 | Haire et al. | |
| 7,061,523 B2 | 6/2006 | Fujita et al. | |
| 7,071,830 B2 | 7/2006 | Sahlberg et al. | |
| 2002/0092346 A1 | 7/2002 | Niekerk et al. | |
| 2002/0092347 A1 | 7/2002 | Niekerk et al. | |
| 2002/0130771 A1 | 9/2002 | Osborne et al. | |
| 2002/0145525 A1 * | 10/2002 | Friedman et al. | 340/573.5 |
| 2004/0061655 A1 | 4/2004 | Forster et al. | |
| 2005/0012616 A1 * | 1/2005 | Forster et al. | 340/572.7 |
| 2005/0156744 A1 * | 7/2005 | Pires | 340/573.5 |
| 2005/0212660 A1 | 9/2005 | Hansen et al. | |
| 2005/0230486 A1 | 10/2005 | Halope | |
| 2005/0231371 A1 | 10/2005 | Rowe | |
| 2005/0242957 A1 | 11/2005 | Lindsay et al. | |
| 2005/0285746 A1 | 12/2005 | Sengupta et al. | |
| 2006/0290501 A1 * | 12/2006 | Hammad et al. | 340/572.1 |

FOREIGN PATENT DOCUMENTS

| | | |
|---|---|---|
| DE | 19525326 C1 | 10/1996 |
| DE | 29813738 U1 | 1/1999 |
| DE | 19742126 A1 | 3/1999 |
| DE | 102004015994 A1 | 11/2005 |
| EP | 1459911 A1 | 9/2004 |
| EP | 1538556 A1 | 8/2005 |
| JP | 2004246816 A | 9/2004 |
| WO | 9614813 A1 | 5/1996 |
| WO | WO 01/80174 A1 | 10/2001 |
| WO | WO 2004/016454 A1 | 2/2004 |
| WO | WO 2004/025554 A1 | 3/2004 |
| WO | WO 2004/046762 A1 | 6/2004 |
| WO | WO 2004/074016 A1 | 9/2004 |
| WO | WO 2005/006243 A2 | 1/2005 |
| WO | WO 2005/070143 A2 | 8/2005 |
| WO | WO 2005/076205 A1 | 8/2005 |
| WO | WO 2005/089143 A2 | 9/2005 |
| WO | WO 2005/109308 A1 | 11/2005 |

OTHER PUBLICATIONS

Doty, F. David, "High Resolution NMR Probes and RF Sample Coils for Liquids," Doty Scientific, Inc.

International Search Report for Application No. PCT/US07/23303.

Written Opinion of the International Searching Authority for Application No. PCT/US07/23303.

\* cited by examiner

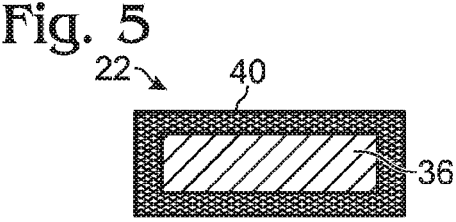
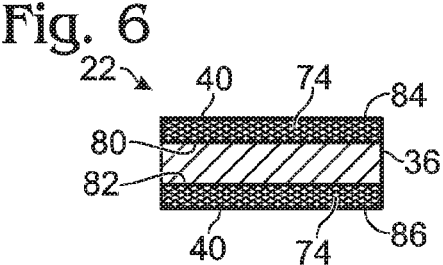
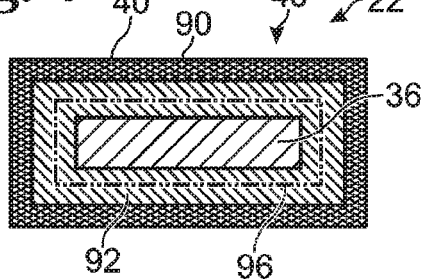
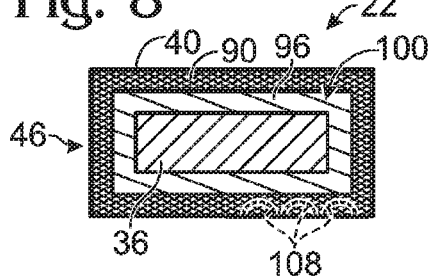
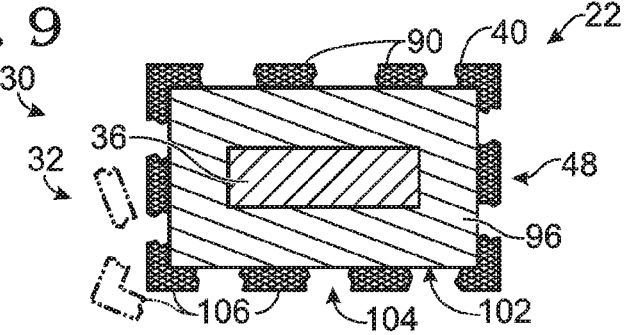
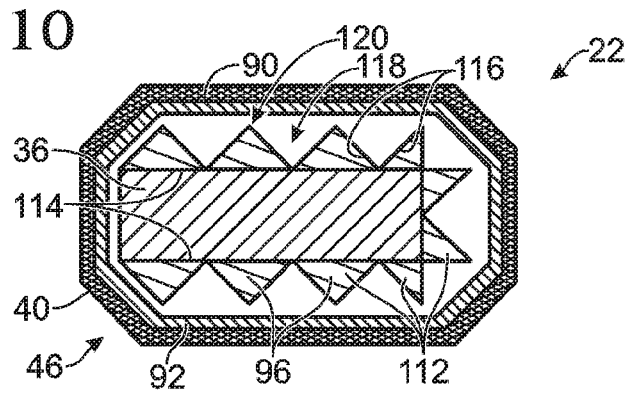
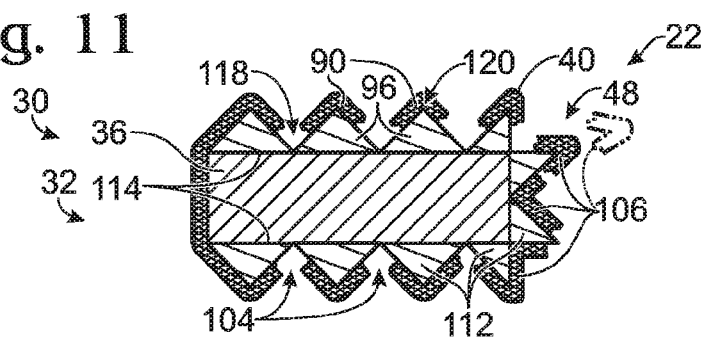

SENSORS AND SYSTEMS FOR DETECTING ENVIRONMENTAL CONDITIONS OR CHANGES

FIELD OF THE DISCLOSURE

The present disclosure relates generally to sensors and systems for detecting environmental conditions or changes.

BACKGROUND OF THE DISCLOSURE

The need to detect environmental conditions or changes arises in many situations. For example, solid materials or liquids may be introduced into or collect within an environment, parts or components of a system may wear down or out, or the temperature, pressure, chemical composition, atmosphere and/or some other environmental condition may change. Regardless of whether such changes or conditions may be beneficial, benign, harmful, desirable and/or undesirable, an indication of the change or condition may be useful. However, such changes or conditions may occur in locations where access is difficult or even impossible, where access, although possible or even simple, is undesirable for any number of reasons, and/or where the environmental conditions or changes may be hazardous to humans and/or equipment.

Nonexclusive illustrative examples of such environmental conditions or changes may include detecting worn-out equipment or materials, detecting leaks in containers carrying a fluid, detecting the presence of fluids in undesirable locations, detecting leaching (leaks of chemicals) in silver or gold mining operations, detecting water or gas line bursts, or the like. Additional examples may include the detection of temperature changes, atmospheric changes (such as changes in pressure and/or composition), the presence or absence of one or more materials, and/or changes in other physical or environmental conditions such as light or noise levels, or wear of mechanical devices, such as brake pads or the like.

Additional nonexclusive illustrative examples of situations in which it would be desirable to detecting environmental conditions or changes arise in the field of health care. For example, the detection of body fluids would be desirable for assisting in the prevention of diaper rash, for potty training of infants, and in curing enuretic youngsters, as well as for detecting the leakage of blood or other fluids after surgery and invasive diagnostic procedures. As a further nonexclusive illustrative example, the detection of incontinence in chronically bedridden persons, such as in the elder care field, would be useful to facilitate better care for chronically bedridden persons.

For example, incontinence is a considerable problem in elder health care. Elders often are immobile, and if these immobile elders become incontinent and lose control of the evacuative functions of urination or defecation and soil themselves, they may be unable to help themselves or seek help. The urine or feces might stay in place long enough for the elder to develop sores, which can result in sickness, infection, and in the worse cases, even death.

The current method of determining whether an elder has lost control of his or her evacuative functions of urination or defecation requires a caregiver to manually check the elder's bedding and/or diaper. This is an arduous and demeaning process, both for the caregiver and for the elder. Thus, there exists a need for an easy and non-intrusive method of detecting incidents of incontinence in elders.

Examples of sensors or systems for detecting predetermined environmental conditions are disclosed in the following U.S. Pat. Nos. 5,557,263; 5,570,082; 5,904,671; 6,294,997; 6,373,395; 6,583,722; 6,774,800; 6,846,994; 6,916,968; 7,053,781; 7,071,830; and U.S. Patent Application Publication Nos. 2004/0061655; 2005/0012616; 2005/0285746. Examples of radio frequency identification (RFID) devices and systems are disclosed in the following U.S. Pat. Nos. 5,904,671; 6,294,997; 6,583,722; 6,774,800; 6,898,489; U.S. Patent Application Publication Nos. 2004/0061655; 2005/0012616; 2005/0285746; and in PCT Publication Nos. WO 99/16019; WO 01/80174; WO 2004/016454; WO 2004/046762; WO 2005/006243; WO 2005/025554; WO 2005/076205; WO 2005/109308. The complete disclosures of these and all other publications referenced herein are incorporated by reference in their entirety for all purposes.

SUMMARY OF THE DISCLOSURE

In one example, a system for detecting a predetermined environmental condition may include a device capable of providing information, a non-human interrogator, and a shield. The interrogator may be configured to read information provided by the device. The shield may have a first condition and a second condition. In the first condition the shield may be configured to preclude the interrogator from reading information provided by the device. In the second condition the shield may be configured to enable the interrogator to read information provided by the device. The shield may be configured to transition from the first condition to the second condition when the shield is exposed to the predetermined environmental condition.

In one example, a system for detecting a predetermined environmental condition may include a first device configured to transmit a first signal, a second device configured to receive a second signal, and a sensor. The sensor may include a third device and a shield disposed proximate the third device. The third device, responsive to receipt of the first signal by the third device, may be configured to transmit the second signal. The shield may be configured to preclude transmission of at least one of the first signal to the third device and the second signal from the third device. The efficacy of the shield may, upon exposure of the shield to the predetermined environmental condition, be sufficiently disrupted such that the disrupted shield may permit transmission of at least one of the first signal to the third device and the second signal from the third device.

In one example, a sensor for detecting a predetermined environmental condition may include a device capable of providing information and a shield disposed proximate the device. The shield may have a first condition and a second condition. In the first condition the shield may be configured to prevent access to information provided by the device. In the second condition the shield may be configured to permit access to information provided by the device. The shield may be configured to transition from the first condition to the second condition when the shield is exposed to the predetermined environmental condition.

In one example, a method of detecting a predetermined environmental condition may include providing a device capable of storing information, which may include predetermined information stored thereon, and a non-human interrogator, which may be configured to read information stored on the device. The method may further include providing a shield. The shield may have a first condition and a second condition. In the first condition the shield may be configured to preclude the interrogator from reading information stored on the device. In the second condition the shield may be configured to enable the interrogator to read information stored on the device. The shield may be provided in the first condition, and the shield may be configured to transition from the first condition to the second condition when the shield is exposed to the predetermined environmental condition. The method may further include exposing the shield to the predetermined environmental condition such that the shield may transition from the first condition to the second condition; reading with the interrogator the predetermined information stored on the device; and indicating that the predetermined environmental condition exists in response to the interrogator reading the predetermined information stored on the device.

BRIEF DESCRIPTION OF THE DRAWINGS

FIG. 5 is a schematic cross-sectional view of an illustrative example of a sensor that has separate shields.

FIG. 6 is a schematic cross-sectional view of an illustrative example of a sensor that has a continuous shield.

FIG. 7 is a schematic cross-sectional view of an illustrative example of a sensor that has a shield that includes a carrier.

FIG. 8 is a schematic cross-sectional view of an illustrative example of a sensor that has an expanding facilitator, with the shield shown in a first or shielding condition.

FIG. 9 is a schematic cross-sectional view of the sensor of FIG. 8, with the shield shown in a second or disrupted condition.

FIG. 10 is a schematic cross-sectional view of an illustrative example of a sensor that has a differential surface area based facilitator, with the shield shown in a first or shielding condition.

FIG. 11 is a schematic cross-sectional view of the sensor of FIG. 10, with the shield shown in a second or disrupted condition.

DETAILED DESCRIPTION

Figure 1:
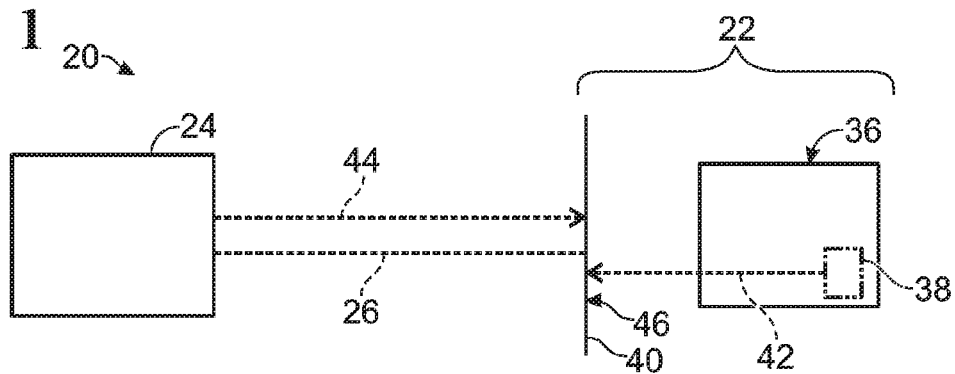
FIG. 1 is a schematic view of an illustrative example of a system for detecting environmental conditions or changes, with the shield shown in a first or shielding condition.
Figure 2:
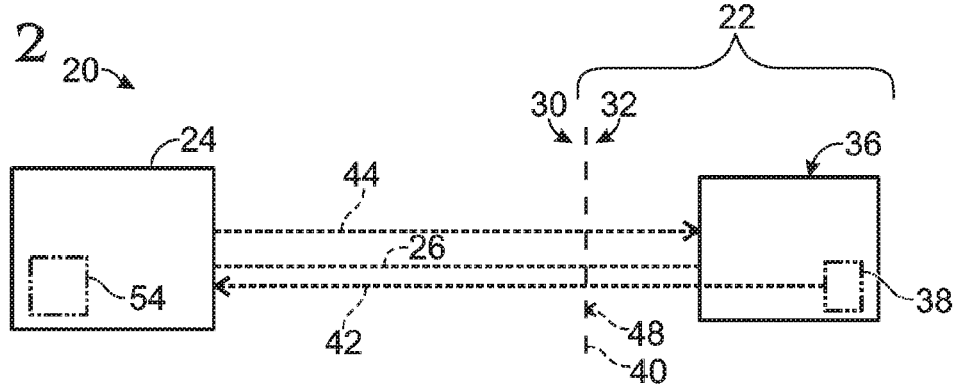
FIG. 2 is a schematic view of the system of FIG. 1, with the shield shown in a second or disrupted condition.

A nonexclusive illustrative example of a system 20 for detecting environmental conditions or changes is shown generally at 20 in FIGS. 1 and 2. Unless otherwise specified, system 20 and its various components may, but are not required to, contain at least one of the structure, components, functionality, and/or variations as the other systems for detecting environmental conditions or changes described and/or illustrated herein. As shown in the nonexclusive illustrative example presented in FIGS. 1 and 2, system 20 includes a sensor 22, a corresponding non-human reader or interrogator 24, and a communication path 26 extending between the sensor 22 and the interrogator 24. When used in combination, sensor 22 and a corresponding appropriately configured interrogator 24 provide a system suitable for detecting at least one predetermined environmental condition 30 or predetermined environmental change 32, as will be more fully described below.

Sensor 22 includes a device 36, which is capable of storing, representing, or providing information 38 in a machine readable format, and a shield 40, which may be disposed proximate device 36. In some nonexclusive illustrative examples, the information 38 that is represented or provided by device 36 may be stored in or on device 36. As used herein, the storage of information refers to any embodiment of data or information in and/or on a tangible object, whether intrinsically, actively or intentionally.

Shield 40 is configured to prevent access to the information 38 stored in or on, represented by or provided by device 36, such as by precluding interrogator 24 from reading the information 38 that is stored in or on, represented by or provided by device 36. For example, shield 40 may at least partially disrupt, interfere with, or interrupt communication path 26, as shown in the schematically represented nonexclusive illustrative example presented in FIG. 1.

A corresponding interrogator 24 for sensor 22 is one that is configured to read or otherwise access the information 38 that is stored in or on, represented by or provided by device 36 in a particular machine readable format. If there is a communications path 26 between interrogator 24 and device 36, interrogator 24 reads or otherwise accesses the information 38 stored in or on, represented by or provided by device 36 when interrogator 24 receives a second or information signal 42 from device 36, such as in response to a first or interrogation signal 44. In some nonexclusive illustrative examples, information signal 42 may at least partially include at least a portion of the information 38 that is stored in or on, represented by or provided by device 36. In some nonexclusive illustrative examples, information signal 42 may at least partially include, or be based on or derived from, at least a portion of interrogation signal 44 that has been at least partially reflected or otherwise retransmitted from device 36. As shown schematically in the nonexclusive illustrative example presented in FIG. 2, interrogation signal 44 may be generated by interrogator 24. However, in some nonexclusive illustrative examples the interrogation signal 44 may be generated externally from interrogator 24.

Information 38 may be stored in or on, represented by or provided by device 36 in any suitable machine readable format. As used herein, machine readable format refers to any format, system, mechanism or manner of embodying, storing, representing or providing data or information in a form that can be accessed, read, sensed, interpreted or otherwise detected by the hardware and/or software of an appropriately configured machine and/or computer. The suitability of a particular machine readable format may be determined based on the nature and suitability of the potentially available communications paths 26 between sensor 22 and interrogator 24. The nature and suitability of the available communications paths 26 may depend on such factors as the quantum of information stored in or on, represented by or provided by device 36, the environment in which device 36 is or is expected to be used, the physical proximity or distance between sensor 22 and interrogator 24, or the like.

In some nonexclusive illustrative examples, when sensor 22 and interrogator 24 are optically visible relative to each other such that there is an optical communication path 26 between sensor 22 and interrogator 24, information 38 may be stored, represented or provided in an optically readable format such as a barcode or any suitable type of machine readable characters or indicia. In some nonexclusive illustrative examples, such as where physical obstructions preclude an optical communication path 26 between sensor 22 and interrogator 24, a magnetic or electromagnetic communication path 26 may exist between sensor 22 and interrogator 24. When a magnetic communication path 26 is used, information 38 may be stored in or on, represented by or provided by a magnetic label or marker and may be detected by an appropriate device such as a Hall effect sensor. When an electromagnetic communication path 26 is used, information may be stored in or on, represented by or provided by an RFID tag, the usage of which will be more fully discussed below. Other nonexclusive illustrative examples of a communication path 26 may be based on acoustics, such as the use of surface acoustic wave devices, or any other suitable mechanism or method that is capable of transmitting information. These and other nonexclusive illustrative examples of communication paths are discussed in Klaus Finkenzeller, RFID HANDBOOK (Rachel Waddington trans., 2d ed. 2003), the complete disclosure of which is incorporated by reference in its entirety for all purposes.

Information 38 may be any quantum of data that is configurable to provide an indication of a detected predetermined environmental condition 30 or predetermined environmental change 32. In some nonexclusive illustrative examples, information 38 may be as simple as a single bit of data, which is sufficient to provide an indication of the existence or absence of the particular predetermined environmental condition 30 or predetermined environmental change 32 that sensor 22 is configured to detect. For example, device 36 may provide information 38 in the form of a simple binary yes/no indication that device 36 is detectable or otherwise readable by interrogator 24, which may correspond to the existence or absence of the particular predetermined environmental condition 30 or predetermined environmental change 32 that sensor 22 is configured to detect. In some nonexclusive illustrative examples, such as in some nonexclusive illustrative examples where information 38 is a simple binary yes/no indication that device 36 is detectable or otherwise readable by interrogator 24, the information 38 may be limited to the existence of the device. In some nonexclusive illustrative examples, such as where device 36 is capable of storing more than a single bit of information, information 38 may be sufficient to provide more than a simple indication of the existence or occurrence of a particular environmental condition or environmental change. For example, information 38 may include any suitable combination of information or data such as location, object or personal identification, details regarding the particular environmental condition or environmental change that exists or has occurred, timing information regarding the duration of the detected environmental condition, elapsed time since the occurrence of the environmental change, or the like.

As shown in the nonexclusive illustrative example presented in FIGS. 1 and 2, shield 40 may be in a shielding or first condition 46 or in a disrupted or second condition 48. When shield 40 is in the first condition 46, shield 40 is configured to prevent access to the information 38 stored in or on, represented by or provided by device 36, such as by precluding interrogator 24 from reading or otherwise accessing the information 38 that is stored in or on, represented by or provided by device 36, such as by at least partially disrupting, interfering with, or interrupting communication path 26, as schematically shown in FIG. 1. For example, when shield 40 is in the first condition 46, shield 40 may at least partially preclude transmission of an interrogation signal 44 from interrogator 24 to device 36 and/or shield 40 may at least partially preclude the transmission of an information signal 42, which may at least partially contain or represent the information 38 stored in or on, represented by or provided by the device 36, from device 36 to the interrogator 24.

The method or mechanism by which shield 40 disrupts, interferes with, or interrupts communication path 26 varies with the nature of the communication path 26, the interrogation signal 44, and information signal 42. For example, if the information 38 stored in or on, represented by or provided by device 36 is optically readable by interrogator 24, then shield 40 might be at least partially opaque to at least one of communication path 26, interrogation signal 44, and information signal 42 when shield 40 is in the first condition 46. If the information 38 stored in or on, represented by or provided by device 36 is magnetically readable by interrogator 24, then shield 40 might be configured to at least partially oppose the magnetic field of the interrogation signal 44 generated by interrogator 24. For example, shield 40 may include a metallic surface positioned adjacent device 36 such that the eddy currents induced in the metallic surface at least partially oppose the magnetic field of the interrogation signal 44. If the information 38 stored in or on, represented by or provided by device 36 is readable by interrogator 24 via electromagnetic coupling between interrogator 24 and device 36, then shield 40 may be configured to at least partially disrupt, interfere with, or interrupt the electromagnetic field generated by interrogator 24, such as where shield 40 acts as a radio frequency (RF) shield when device 36 is an RFID transponder. The use and operational principles of RF shields are known, and will not be discussed in detail here.

When shield 40 is in the second condition 48, shield 40 is configured to permit access to the information 38 stored in or on, represented by or provided by device 36, such as by enabling or permitting interrogator 24 to read or otherwise access the information 38 that is stored in or on, represented by or provided by device 36, such as by permitting communication path 26 to extend from interrogator 24 to device 36, as schematically shown in FIG. 2. For example, when shield 40 is in the second condition 48, the efficacy of shield 40 is sufficiently disrupted such that the disrupted shield 40 permits transmission of the interrogation signal 44 from interrogator 24 to device 36 and/or the disrupted shield 40 permits transmission of the information signal 42 and/or the information 38 stored in or on, represented by or provided by the device 36 from device 36 to the interrogator 24.

System 20 detects environmental conditions or changes based on the transition of shield 40 between the first condition 46 and the second condition 48. In particular, as shown in the nonexclusive illustrative example presented in FIGS. 1 and 2, shield 40 is configured such that exposure to a predetermined environmental condition 30 or predetermined environmental change 32 sufficiently disrupts shield 40 such that shield 40 transitions from first condition 46 to second condition 48, which permits transmission of the interrogation signal 44 from interrogator 24 to device 36 and transmission of the information signal 42 and/or the information 38 stored in or on, represented by or provided by the device 36 from device 36 to the interrogator 24. When interrogator 24 receives information signal 42 and/or information 38 from device 36, system 20 provides an indication 54 of the predetermined environmental condition 30 or predetermined environmental change 32. In some nonexclusive illustrative examples, the complexity of indication 54 may vary with the complexity of information 38 stored in or on, represented by or provided by device 36 as well as with the ability of interrogator 24 to access information 38.

The particular predetermined environmental condition or change to which a particular sensor is responsive may be determined by selecting a shield that has a shielding efficacy that will be disrupted when the shield is exposed to a particular condition or change. As nonexclusive illustrative examples, a soluble shield may be used when it is desired to detect the presence of a particular solvent, a shield that degrades or otherwise changes properties at certain temperatures may be used when it is desired to detect a particular temperature, or a selectively positioned material having low mechanical durability may be used when it is desired to detect mechanical wear beyond a certain threshold. In some nonexclusive illustrative examples, a shield may be selected based on its nonresponsiveness to a particular predetermined environmental condition or change whose detection is not desired. For example, if it is desired to detect temperature variations, but not the presence of a solvent, an insoluble shield that degrades at certain temperatures may be used.

In some nonexclusive illustrative examples, disruption of the shielding efficacy of a particular shield 40 or shielding material when the shield 40 transitions from a first or shielding condition 46 to a second or disrupted condition 48 may not correspond to mechanical disruption or damage to the shield or shielding material. In such an example, only the particular physical property that corresponds to shielding efficacy needs to be disrupted or altered. As a nonexclusive illustrative example, shield 40 may include an environmentally responsive liquid crystal material that is capable of at least partially disrupting, interfering with, or interrupting communication path 26 when the liquid crystal material is exposed to a predetermined environmental condition 30 or predetermined environmental change 32. For example, where the information 38 stored in or on, represented by or provided by device 36 is optically readable by interrogator 24, shield 40 might be an environmentally responsive liquid crystal material that transitions from an at least partially opaque condition to an at least partially transparent condition when shield 40 transitions from first condition 46 to second condition 48 upon exposure to predetermined environmental condition 30 or predetermined environmental change 32.

In some nonexclusive illustrative examples, system 20 may be configured to only provide an indication that sensor 22 has been exposed to predetermined environmental condition 30 or predetermined environmental change 32. For example, shield 40 may be configured such that exposure to predetermined environmental condition 30 or predetermined environmental change 32 irreversibly disrupts shield 40 such that shield 40 is permanently transitioned from first condition 46 to second condition 48. In such an example, sensor 22 may be considered a single-use sensor, which must be replaced after use, or device 36 may be provided with a new shield 40 such the sensor 22 is at least partially reusable.

In some nonexclusive illustrative examples, system 20 may be configured to provide an indication that sensor 22 has not been exposed to predetermined environmental condition 30 or predetermined environmental change 32. For example, system 20 may be configured to provide an indication that sensor 22 has not been exposed to predetermined environmental condition 30 or predetermined environmental change 32 when interrogator 24 has not received information signal 42 and/or information 38 from device 36 because shield 40 has not transitioned from first condition 46 to second condition 48.

In some nonexclusive illustrative examples, system 20 may be configured to provide an indication that sensor 22 is not currently exposed to and/or has previously been exposed to predetermined environmental condition 30 or predetermined environmental change 32. For example, shield 40 may be configured to transition from second condition 48 to first condition 46 when shield 40 is no longer exposed to predetermined environmental condition 30 or predetermined environmental change 32, such as where shield 40 is configured to reversibly transition between first condition 46 and second condition 48. In such an example, system 20 may be configured to provide an indication that sensor 22 is not currently exposed to and/or has previously been exposed to predetermined environmental condition 30 or predetermined environmental change 32 when interrogator 24 has previously received, but is not currently receiving, information signal 42 and/or information 38 from device 36, such as where the efficacy of shield 40 is at least partially restored when shield 40 is no longer exposed to predetermined environmental condition 30 or predetermined environmental change 32.

Figure 3:
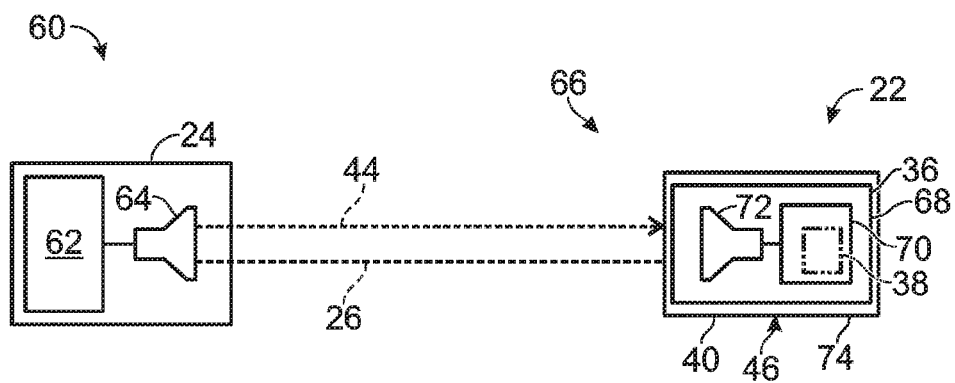
FIG. 3 is a schematic view of an illustrative example of an RFID-based system for detecting environmental conditions or changes, with the shield shown in a first or shielding condition.
Figure 4:
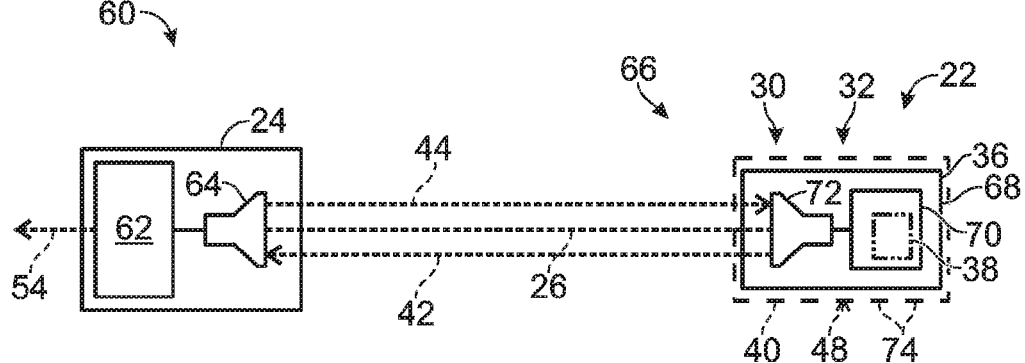
FIG. 4 is a schematic view of the RFID-based system of FIG. 3, with the shield shown in a second or disrupted condition.

A nonexclusive illustrative example of an RFID-based system 60 for detecting environmental conditions or changes is shown generally at 60 in FIGS. 3 and 4. Unless otherwise specified, system 60 and its various components may, but are not required to, contain at least one of the structure, components, functionality, and/or variations as the other systems for detecting environmental conditions or changes described and/or illustrated herein. As shown in the nonexclusive illustrative example presented in FIGS. 3 and 4, RFID-based system 60 may include an interrogator 24, a corresponding sensor 22, and a shield 40, all of which are configured for use within an RFID-based system.

Nonexclusive illustrative examples of RFID technologies and systems that are suitable for use with the RFID-based system 60 may be classified based on the type of coupling and/or communication path 26 that exists between interrogator 24 and transponder or device 36. Such nonexclusive illustrative examples may include inductive coupling, electromagnetic backscatter coupling, close coupling, electrical coupling, or the like. The use and operational principles of such RFID technologies and systems are known, and will not be discussed in detail here. Further discussion of RFID technologies and systems may be found in Klaus Finkenzeller, RFID HANDBOOK (Rachel Waddington trans., 2d ed. 2003), the complete disclosure of which is incorporated by reference in its entirety for all purposes As shown in the nonexclusive illustrative example presented in FIGS. 3 and 4, when used with an RFID-based system 60, interrogator 24 includes an RFID reader 62 that is coupled to an antenna 64. Antenna 64 is configured to transmit an interrogation signal 44, such as when the RFID reader 62 generates an electromagnetic field within an interrogation zone 66. In some nonexclusive illustrative examples, RFID reader 62 may continuously generate an electromagnetic field within interrogation zone 66. RFID reader 62 is also configured to receive a second or information signal 42, such as when an RFID-based sensor 22 is disposed within interrogation zone 66.

As shown in the nonexclusive illustrative example presented in FIGS. 3 and 4, when used with an RFID-based system 60, sensor 22 may include device 36, which may be included in the RFID transponder 68. Device 36 may include a data carrier 70, such as a microchip, which is coupled to a suitable coupling element 72, such as a coil or an antenna. In some nonexclusive illustrative examples, data carrier 70 may be conductively coupled to coupling element 72. When the shield 40 is in the second condition 48, RFID transponder 68 is configured to transmit information signal 42, and/or the information 38 that is stored in or on, represented by or provided by data carrier 70, to the RFID reader 62 of interrogator 24 in response to RFID transponder 68 receiving an interrogation signal 44 from interrogator 24. In some nonexclusive illustrative examples, information signal 42 may at least partially include, or be based on or derived from, at least a portion of interrogation signal 44 that has been at least partially reflected or otherwise retransmitted from device 36. For example, RFID transponder 68 may be configured to reflect back to the interrogator 24 at least a portion of the electromagnetic field that corresponds to the interrogation signal 44. In some nonexclusive illustrative examples, an information signal 42 based on a reflected portion of interrogation signal 44 may provide a simple binary yes/no indication that device 36 is detectable or otherwise readable by interrogator 24, which may correspond to the existence or absence of the particular predetermined environmental condition 30 or predetermined environmental change 32 that sensor 22 is configured to detect. In some nonexclusive illustrative examples, information signal 42 may at least partially carry information 38 in the form of a modulation imposed on a reflected portion of the interrogation signal 44, such as due to modulation of the reflection cross-section of RFID transponder 68. When RFID transponder 68 is passive, such as when RFID transponder 68 does not include its own power source, the interrogation signal 44 that is transmitted by interrogator 24 may provide operating power to RFID transponder 68.

As shown in the nonexclusive illustrative example presented in FIG. 3, when used with an RFID-based system 60, shield 40 may be configured to preclude access to the information 38 stored in or on, represented by or provided by device 36 when shield 40 is in the first condition 46. For example, when shield 40 is in the first condition 46, shield 40 at least partially disrupts, interferes with, or interrupts RF-based communication path 26, which precludes interrogator 24 from reading the information 38 that is stored in or on, represented by or provided by device 36, such as by precluding interrogator 24 from transmitting interrogation signal 44 or power to device 22, by precluding device 22 from receiving interrogation signal 44 or power from interrogator 24, and/or by precluding device 22 from transmitting information signal 42.

When used with an RFID-based system 60, shield 40 may include any material or configuration capable of at least partially disrupting, interfering with, or interrupting the RF-based communication path 26 that exists between interrogator 24 and device 36, such as between antenna 64 and coupling element 72. For example, shield 40 may include a material capable of providing electromagnetic or RF shielding, such as a conductive material disposed between interrogator 24 and device 36, such as where shield 40 includes a conductive material 74 that at least partially surrounds device 36 and/or coupling element 72. In some nonexclusive illustrative examples, conductive material 74 may at least partially form a Faraday cage around device 36 and/or coupling element 72. Nonexclusive illustrative examples of suitable conductive materials 74 include conductive sheets, conductive meshes, conductive greases, paints or ink, and the like. Nonexclusive illustrative examples of conductive sheets may include metal foils, such as gold or aluminum foils, carbon-based sheets, such as those based on carbon fibers, and the like. Nonexclusive illustrative examples of conductive meshes may include metallic meshes, carbon-based meshes, and the like.

Schematic cross-sectional views of nonexclusive illustrative examples of sensors 22 and shields 40 are shown in FIGS. 5-11. Unless otherwise specified, each of the sensors 22 shown in FIGS. 5-11 may, but are not required to, contain at least one of the structure, components, functionality, and/or variations as the other sensors described and/or illustrated herein.

As shown in the nonexclusive illustrative example presented in FIG. 5, shield 40 may completely surround device 36. For example, as discussed above, shield 40 may be in the form of a Faraday cage, such as where a conductive material 74 completely or nearly completely surrounds device 36.

In some nonexclusive illustrative examples, shield 40 may not completely surround device 36. For example, as shown in the nonexclusive illustrative example presented in FIG. 6, sensor 22 may include a device 36 that has first and second opposed major sides, faces or surfaces 80, 82. In such an example, shield 40 includes first and second portions 84, 86 of conductive material 74 that are disposed on the respective first and second opposed major sides, faces or surfaces 80, 82 of device 36.

In some nonexclusive illustrative examples, the predetermined environmental condition 30 or predetermined environmental change 32 that system 20 is configured to detect may include the presence of a predetermined fluid. In such an example, at least a portion of shield 40 exhibits a response when exposed to the fluid. For example, at least a portion of shield 40 may chemically respond when exposed to the fluid, such as where at least a portion of shield 40 is at least partially soluble or otherwise subject to breakdown when exposed to the predetermined fluid. Such an at least partially soluble shield 40 may be configured to at least partially transition from the first or shielding condition 46 to the second or disrupted condition 48 when shield 40 is exposed to the predetermined fluid. For example, at least a portion of an at least partially soluble shield may dissolve when the shield is exposed to the predetermined fluid, which may enable the transition of shield 40 from the first or shielding condition 46 to the second or disrupted condition 48, such as by sufficiently disrupting the efficacy of shield 40 such that there is a communication path 26 extending from interrogator 24 to device 36, as suggested in FIG. 2. In some nonexclusive illustrative examples, at least a portion of shield 40 may otherwise respond when exposed to the predetermined fluid such as by hardening, swelling, or the like.

In some nonexclusive illustrative examples, an at least partially soluble shield 40 may include a shielding layer 90 that is at least partially disposed on a carrier material 92, as shown in FIG. 7. The shielding layer 90 may be configured such that, when shield 40 is in the first condition 46, shielding layer 90 prevents access to the information 38 stored in or on, represented by or provided by device 36, such as by precluding interrogator 24 from reading the information 38 that is stored in or on, represented by or provided by device 36, such as by at least partially disrupting, interfering with, or interrupting communication path 26, as schematically shown in FIG. 1. For example, when shield 40 is in the first condition 46, shielding layer 90 may at least partially preclude transmission of an interrogation signal 44 from interrogator 24 to device 36 and/or shielding layer 90 may at least partially preclude the transmission of an information signal 42, which may at least partially contain or represent the information 38 stored in or on, represented by or provided by the device 36, from device 36 to the interrogator 24.

The use of a carrier material may permit or simplify the use of particular shielding materials for shielding layer 90. For example, such as in the case of an RFID-based system, shielding layer 90 may be in the form of a conductive ink, grease or paint that is printed or otherwise deposited onto the carrier material 92. In such an example, the structural integrity of shield 40 may be provided by the carrier material 92 while the shielding efficacy may be provided by the shielding layer 90. Even though the shielding material itself may be relatively insoluble or otherwise unresponsive to the presence of the predetermined environmental condition 30, predetermined environmental change 32, or predetermined fluid to which shield 40 is exposed, the carrier material 92 itself may be at least partially soluble or otherwise subject to breakdown when so exposed. Thus, because the structural integrity of shield 40 is provided by the carrier material 92, the breakdown of carrier material 92 may at least partially disrupt shielding layer 90 and cause the transition of shield 40 from the first or shielding condition 46 to the second or disrupted condition 48 when shield 40 is exposed to predetermined environmental condition 30, predetermined environmental change 32, or the predetermined fluid.

When sensor 22 is configured for use in the detection of a water-based fluid, examples of suitable materials for carrier material 92 may include a water-soluble polymer such as polyvinyl alcohol (PVA). Other water-soluble materials such as soluble rice paper or the like may also be used.

In some nonexclusive illustrative examples, the at least partially soluble shield 40 of sensor 22 may be configured such that its solubility is at least partially temperature dependent. For example, the water solubility of a water-soluble carrier material 92 may be changed by changing the molecular weight of a polymer utilized in the carrier material, such as by controlling crosslinking of the polymer. By increasing crosslinking of the polymer by a suitable amount, such as by a several-fold increase in molecular weight, the water-soluble material may become substantially insoluble in cold water, but still may remain soluble in hot water.

In some nonexclusive illustrative examples where an RFID-based system 60 is configured to detect the presence of a predetermined fluid, shielding layer 90 may include a conductive material that has its conductivity characteristics altered by exposure to a predetermined substance or chemical. For example, shielding layer 90 may include a conductive material whose conductance is reduced or eliminated when the conductive material is exposed to a predetermined fluid such as water or a fluid that is discharged during an incontinence event, such as urine.

In addition to use with at least partially soluble shields, a shielding layer 90 may be used in sensors configured to detect mechanical changes. As a nonexclusive illustrative example, a shielding layer 90, such as a metal foil in the case of an RFID-based system 60, may be selectively placed within a component that is subject to mechanical wear or chemically induced reductions to structural volume. A nonexclusive illustrative example of such use of a shielding layer 90 would be the inclusion of sensor 22 within a friction-inducing component, such as one tending to decrease in thickness during use, such as a brake pad. By placing sensor 22 at a predetermined depth in such a component, wear of the component to the predetermined depth will expose the shielding layer 90 of the sensor to wear. In such an example, use of a shielding layer 90 that has little resistance to wear, such as a metal foil in the case of an RFID-based system 60, will cause the shield 40 to quickly transition from the first condition 46 to the second condition 48 such that the system 60 will detect the wear of the component to the predetermined depth.

In some nonexclusive illustrative examples, sensor 22 may include a facilitator 96 configured to at least partially ensure, stimulate, accelerate or otherwise enable the transition of shield 40 from the first or shielding condition 46 to the second or disrupted condition 48 when sensor 22 and/or shield 40 is exposed to predetermined environmental condition 30 or the predetermined environmental change 32. Unless otherwise specified, each of the facilitators 96 described herein may, but are not required to, contain at least one of the structure, components, functionality, and/or variations as the other facilitators described and/or illustrated herein. The facilitator 96 may be any material, structure, or mechanism capable of at least partially enabling the transition of shield 40 from the first or shielding condition 46 to the second or disrupted condition 48 when sensor 22 and/or shield 40 is exposed to the predetermined environmental condition 30 or the predetermined environmental change 32. For example, by expanding, contracting, and/or mechanically or chemically interacting with the environment, facilitator 96 may enable the transition of shield 40 from the first or shielding condition 46 to the second or disrupted condition 48, such as by sufficiently disrupting the efficacy of shield 40 such that a communication path 26 is enabled from interrogator 24 to device 36, as suggested in FIG. 2. Nonexclusive illustrative examples of mechanisms by which facilitator 96 may mechanically or chemically interact with the environment may include melting, swelling, charring, dissolving, or otherwise decomposing. In some nonexclusive illustrative examples, facilitator 96 may be configured to ensure the transition of shield 40 from the first or shielding condition 46 to the second or disrupted condition 48 when sensor 22 and/or shield 40 is exposed to the predetermined environmental condition 30 or the predetermined environmental change 32.

In some nonexclusive illustrative examples, the facilitator 96 may be at least partially enclosed by, or integral with, the shielding layer 90 and/or carrier material 92. For example, as suggested in the nonexclusive illustrative example presented in FIG. 7, facilitator 96 may be at least partially disposed within, or be a part of, carrier material 92. In such examples, facilitator 96 may be at least partially formed from a material that is non-shielding relative to device 36. For example, when sensor 22 is used in an RFID-based system 60, facilitator 96 may be fabricated from a suitable non-conducting material such as a plastic, a glass, a ceramic, or the like.

In some nonexclusive illustrative examples, facilitator 96 may be configured to expand or increase in volume when sensor 22 is exposed to predetermined environmental condition 30 or predetermined environmental change 32. For example, facilitator 96 may be configured to expand or increase in volume when shield 40 is exposed to a predetermined fluid. In some nonexclusive illustrative examples, facilitator 96 may include a carrier material 92 that at least partially encloses device 36, with shielding layer 90 enclosing at least a portion of device 36 and at least a portion of facilitator 96. A facilitator 96 that is configured to expand or increase in volume when sensor 22 is exposed to predetermined environmental condition 30 or the predetermined environmental change 32 may be distinct from but within or enclosed by carrier material 92, or the carrier material 92 may itself be configured to expand or increase in volume when it is exposed to predetermined environmental condition 30 or the predetermined environmental change 32.

As shown in the nonexclusive illustrative example presented in FIGS. 8 and 9, at least a portion of shield 40, such as at least a portion of shielding layer 90, including any associated carrier material 92, may enclose a facilitator 96 that is configured to expand or increase in volume when sensor 22 is exposed to predetermined environmental condition 30 or predetermined environmental change 32. In such an example, when facilitator 96 is in a first or unexpanded condition 100, shielding layer 90 is sufficiently intact such that shield 40 is in the first or shielding condition 46, as shown in FIG. 8. When sensor 22 and/or facilitator 96 are exposed to predetermined environmental condition 30 or predetermined environmental change 32, such as to a predetermined fluid, facilitator 96 increases in volume and transitions from first condition 100 to a second or expanded condition 102, as shown in FIG. 9. The increase in volume of facilitator 96 when it is exposed to the predetermined environmental condition or change induces stresses in the shielding layer 90 that are sufficient to at least partially disrupt or rupture the shielding layer 90, such as by formation of gaps 104 in the shielding layer 90, which may cause the transition of shield 40 from the first or shielding condition 46 to the second or disrupted condition 48. The presence of gaps 104 in the shielding layer 90 may alone be sufficient to cause the transition of shield 40 from the first or shielding condition 46 to the second or disrupted condition 48. However, in some nonexclusive illustrative examples, the transition of shield 40 from the first or shielding condition 46 to the second or disrupted condition 48 may occur when the fragments 106 of the shielding layer 90 slough off or otherwise separate from sensor 22, as indicated in FIG. 9. In some nonexclusive illustrative examples, environmental conditions may assist or enhance the separation of fragments 106 from sensor 22. For example, fluid flow, which may be turbulent, proximate sensor 22 may assist or enhance the separation of fragments 106 from sensor 22.

Nonexclusive illustrative examples of suitable materials for a facilitator 96 that is configured to expand or increase in volume when sensor 22 is exposed to predetermined environmental condition 30 or the predetermined environmental change 32 include those materials that provide an expansion large enough to induces stresses in the shielding layer 90 that are sufficient to at least partially disrupt or rupture the shielding layer 90. For example, when used with a sensor 22 configured to detect the presence of a fluid, facilitator may be in the form of a compressed sponge or other material or object tending to expand in response to absorption of the fluid. For example, facilitator 96 may be an absorbent polymer, such as a high-gelling capacity crosslinked salt of polyacrylic acid, such as sodium polyacrylate, which is a crosslinked acrylic acid polymersodium salt.

In some nonexclusive illustrative examples of sensor 22, facilitator 96 may be configured to expand or increase in volume based on a chemical reaction. For example, facilitator 96 may be configured to undergo a chemical reaction when sensor 22 and/or facilitator 96 are exposed to the predetermined environmental condition 30 or the predetermined environmental change 32. Such a chemical reaction may be one that expansively produces a gas. For example, when used with a sensor 22 configured to detect the presence of a fluid, facilitator 96 may be configured to react with the fluid in a chemical reaction that produces a gaseous product. For example, facilitator 96 may include a mixture of citric acid and sodium bicarbonate, which react vigorously to produce carbon dioxide when mixed in a fluid such as water.

In some nonexclusive illustrative examples of sensor 22, such as where sensor 22 includes an expanding facilitator 96 as described above, shielding layer 90 may include at least one stress enhancer 108, as indicated in FIG. 8. In such an example, shield 40 is configured such that at least one stress enhancer 108 induces stress concentrations within the shielding layer 90 when the expanding facilitator 96 increases in volume. Such stress concentrations within the shielding layer 90 may be sufficient to at least partially enable rupture of the shielding layer 90 and enable the transition of shield 40 from the first or shielding condition 46 to the second or disrupted condition 48. For example, as indicated in FIG. 8, at least one stress enhancer 108 may be provided on shielding layer 90 in the form of regions of reduced thickness. Such regions of reduced thickness will lead to locally higher tensile stresses when the shielding layer is stretched over the expanded facilitator 96 when the facilitator is in the second or expanded condition.

In some nonexclusive illustrative examples, facilitator 96 may be configured to mechanically ensure the disruption of shielding layer 90 when sensor 22 and/or shield 40 are exposed to predetermined environmental condition 30 or the predetermined environmental change 32. For example, as schematically represented in the nonexclusive illustrative example presented in FIGS. 10 and 11, facilitator 96 may include a plurality of ridges or projections 112. Ridges or projections 112 may be formed in any suitable pattern. For example, ridges or projections 112 may include a series of two-dimensional projections in the form of linear or curvilinear ridges, which may intersect and/or be parallel. Ridges or projections 112 may alternately or additionally include an array or other distribution of a series of generally one-dimensional projections such as generally pyramidal or conical shapes. Ridges or projections 112 may be at least partially formed from a material that is non-shielding relative to device 36. For example, when sensor 22 is used in an RFID-based system 60, the ridges or projections 112 may be fabricated from a suitable non-conducting material such as a plastic, a glass, a ceramic, or the like.

A facilitator 96 that includes a plurality of ridges or projections 112, may be used with a shield 40 that has a shielding layer 90 deposited on a carrier material 92, such as where shielding layer 90 includes a conductive ink or the like printed onto carrier material 92, as schematically represented in FIG. 10. As discussed above, the structural integrity of such a shield may be provided by the carrier material 92 while the shielding efficacy may be provided by the shielding layer 90. For example, the thicknesses of shielding layer 90 may be significantly larger than the thickness of carrier material 92. By way of nonexclusive illustrative example, carrier material 92 may have a thickness of approximately 0.003 inches (76 μm) while shielding layer 90 may have a thickness of approximately 0.0005 inches (12 μm).

Although the at least partial dissolution or breakdown of carrier material 92 may disrupt shielding layer 90 to a sufficient extent as to cause shield 40 to transition from the first or shielding condition 46 to the second or disrupted condition 48 when shield 40 is exposed to predetermined environmental condition 30 or predetermined environmental change 32, the inclusion of a facilitator 96 that includes a plurality of ridges or projections 112 may ensure that shielding layer 90 is sufficiently disrupted to transition shield 40 to the second or disrupted condition 48. In particular, the plurality of ridges or projections 112 may prevent shielding layer 90 from depositing or decaling itself onto the surfaces 114 of device 36 subsequent to the dissolution or breakdown of carrier material 92. As may be observed from the schematic representation of the nonexclusive illustrative example presented in FIG. 10, the surface area of the exterior surfaces 116 of the plurality of ridges or projections 112 is significantly larger than the surface area of the shielding layer 90 due to the fact that shielding layer 90 passes across the valleys 118 between the ridges or projections 112. Thus, in the event that shielding layer 90 tends to deposit or decal itself onto the plurality of ridges or projections 112 upon the dissolution or breakdown of carrier material 92, shielding layer 90 may be disrupted into fragments 106 that are separated by gaps 104. Shielding layer 90 may be disrupted into fragments 106 because shielding layer 90 lacks sufficient material to deposit or decal itself over the entirety of the surfaces 116 of the peaks 120 and valleys 118 of the ridges or projections 112 without rupturing, as schematically represented in FIG. 11. By way of nonexclusive illustrative example, the depths of the valleys 118 between the ridges or projections 112 may be approximately 0.063 inches (1.6 mm or 1600 μm).

Figure 12:
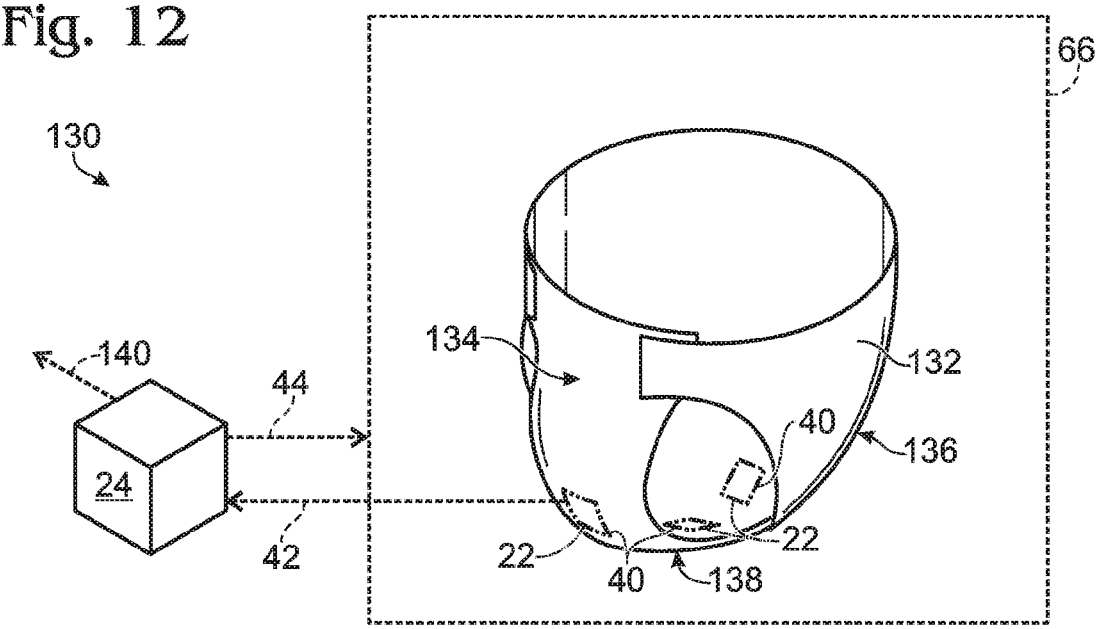
FIG. 12 is a schematic view of an illustrative example of the components of a system for detecting the occurrence of an incontinence event.

A nonexclusive illustrative example of a system for detecting the occurrence of an incontinence event is shown generally at 130 in FIG. 12. Unless otherwise specified, system 130 and its various components may, but are not required to, contain at least one of the structure, components, functionality, and/or variations described and/or illustrated herein. As discussed above, system 130 is based on at least one sensor 22 that is paired with at least one corresponding interrogator 24, which is configured to read information that is stored in or on, represented by, or provided by sensor 22 when its shield 40 is disrupted. System 130 may include a diaper 132 and an interrogator 24.

As shown in the nonexclusive illustrative example presented in FIG. 12, diaper 132 may include at least one sensor 22. The sensors 22 may be disposed within diaper 132 such that the sensors are suitably located to detect a fluid, such as urine or fecal matter, discharged by a patient during an incontinence event. For example, at least one sensor 22 may be located proximate a frontal region 134 of diaper 132, at least one sensor 22 may be located proximate a posterior region 136 of diaper 132, and/or at least one sensor 22 may be located proximate a lower region 138 of diaper 132. In some nonexclusive examples, diaper 132 may be configured such that, when diaper 132 is worn by a patient, at least one sensor 22, and/or its corresponding shield 40, is located proximate a urine discharge orifice and/or proximate a fecal discharge orifice of the patient.

During operation of system 130, a patient may be fitted with a diaper 132 that includes at least one suitably located sensor 22. The patient may be located such that the patient, or at least diaper 132, is positioned within the interrogation zone 66 of interrogator 24. In some nonexclusive illustrative examples, the interrogator 24 may continuously transmit an interrogation signal 44 into the interrogation zone 66. For example, if system 130 is RFID-based, interrogator 24 may continuously generate an electromagnetic field within interrogation zone 66. When the patient experiences an incontinence event, the discharged fluids may be collected in diaper 132 proximate at least one of the sensors 22 and/or its corresponding shield 40. The presence of the discharged fluid proximate the sensor 22 and/or its shield 40, may disrupt the shield 40 such that, responsive to the interrogation signal 44, the sensor 22 may transmit an information signal 42 to the interrogator 24, which may provide an indication 140 of the occurrence of the incontinence event. In some nonexclusive illustrative examples, information signal 42 may provide an indication of the type of incontinence event or it may provide identification and location information.

A nonexclusive illustrative example of an installed system for detecting the occurrence of an incontinence event is shown generally at 150 in FIG. 12. Unless otherwise specified, system 150 and its various components may, but are not required to, contain at least one of the structure, components, functionality, and/or variations as the other systems for detecting the occurrence of an incontinence event described and/or illustrated herein. System 150 may be installed in a fixed location such as a hospital or nursing home room 152.

System 150 may include at least one interrogator 24 mounted or otherwise disposed within the room 152. In some nonexclusive illustrative examples of system 150, at least one interrogator 24 may be configured to continuously transmit an interrogation signal 44 into a fixed interrogation zone 66, such as a zone generally surrounding the bed 154 in which the individual receiving care or patient 156 is located. For example, at least one interrogator 24 may be fixedly mounted within the room 152 or the bed 154. In some nonexclusive illustrative examples, system 150 may be RFID-based, in which case interrogator 24 may continuously generate an electromagnetic field within interrogation zone 66.

In some nonexclusive illustrative examples of system 150, at least one interrogator 24 may be portable, such as to permit usage outside a fixed interrogation zone. In some nonexclusive illustrative examples, at least one interrogator 24 may be fixedly mounted to bed 154.

In some nonexclusive illustrative examples of system 150, at least one sensor 22 may be mounted within the room 152, such as in a piece of furniture or other location in which the patient 156 may experience an incontinence event. For example, as shown in the nonexclusive illustrative example presented in FIG. 13, at least one sensor 22 may be mounted in bed 154, such as within the mattress or sheets.

Figure 13:
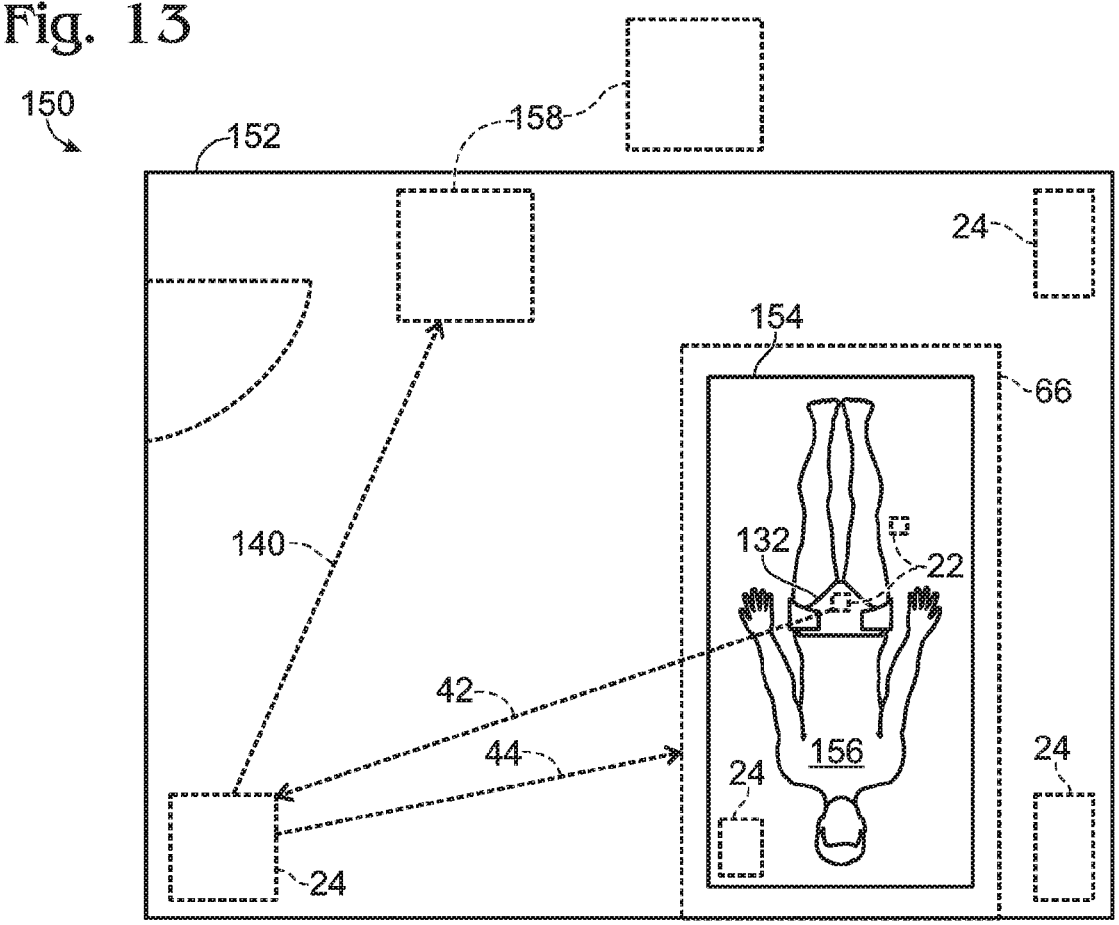
FIG. 13 is a schematic view of an illustrative example of the components of an installed system for detecting the occurrence of an incontinence event.

As shown in the nonexclusive illustrative example presented in FIG. 13, system 150 may include at least one monitoring station 158. Monitoring station 158 may be located at any suitable location where it can receive an indication 140 from at least one of the interrogators 24 that the patient 156 has experienced an incontinence event. Monitoring station 158 may be configured to notify an appropriate party, such as an attendant or nurse, that the patient 156 has experienced an incontinence event. The use of system 150 to provide notification that a patient 156 has experienced an incontinence event may permit an attendant or nurse to become aware of the occurrence of an incontinence event without having to manually examine the patient, which may permit enhanced patient privacy or dignity.

As a nonexclusive illustrative example of operation of a system for detecting environmental conditions or changes, a sensor such as a device capable of storing, representing, or providing information may be provided. In some nonexclusive illustrative examples, the device may be provided with predetermined information stored thereon. The predetermined information may include any suitable combination of information such as location, object or personal identification, details regarding the particular environmental condition or environmental change that exists or has occurred, timing information regarding the duration of the detected environmental condition, elapsed time since the occurrence of the environmental change, or the like.

A non-human interrogator that is configured to read information stored in or on, represented by or provided by the device may be provided. In the case of an RFID-based system for detecting environmental conditions or changes, the interrogator may continuously generate an electromagnetic field within an interrogation zone.

A shield that has a first condition and a second condition may be provided with the shield provided in the first condition. In some nonexclusive illustrative examples, the shield may be provided proximate the device. In the first condition the shield is configured to preclude the interrogator from reading information stored in or on, represented by or provided by the device. In the second condition the shield is configured to enable the interrogator to read information stored in or on, represented by or provided by the device. The shield is configured to transition from the first condition to the second condition when the shield is exposed to a predetermined environmental condition or change, such as the presence of a predetermined fluid.

During operation of the system, the sensor may be placed into an environment in which there is an interest in detecting environmental conditions or changes, such as a predetermined environmental condition or change, such as the presence of a unexpected and/or undesirable material, such as the presence of an unexpected and/or undesirable fluid. The interrogator may be positioned such that, if it could read the information stored in or on, represented by or provided by the device, it would read the information stored in or on, represented by or provided by the device. The interrogator will attempt to read the information stored in or on, represented by or provided by the device. In the case of an RFID-based system for detecting environmental conditions or changes, the interrogator may continuously attempt to read the information stored in or on, represented by or provided by a device located within the interrogation zone. The failure of the interrogator to read the information stored in or on, represented by or provided by the device may be used as an indication that the shield is in the first condition because the predetermined environmental condition or change has not occurred and/or is not currently occurring.

When the shield and/or the sensor are exposed to the predetermined environmental condition or change, the shield will transition from the first condition to the second condition. Once the shield is in the second condition, the interrogator will be able to read the information stored in or on, represented by or provided by the device, and the interrogator will read the information that is stored in or on, represented by or provided by the device. Based on the information read by the interrogator from the device, the interrogator may provide an indication that the predetermined environmental condition or change exists and/or has occurred.

In some nonexclusive illustrative examples of using the system for detecting environmental conditions or changes where the system is being used to provide an indication that a person has experienced an incontinence event, the method may include positioning at least one of the sensor and/or the shield proximate at least one of a urine discharge orifice and/or a fecal discharge orifice of a patient. In such an example, the predetermined fluid includes a fluid discharged by the patient during an incontinence event, such as urine or fecal matter.

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the disclosure includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

We claim:

1. A system for detecting a predetermined environmental condition, wherein the system comprises:
   a device capable of providing information, wherein the device comprises a passive RFID transponder;
   a non-human interrogator configured to read information provided by the device, wherein the interrogator comprises an RFID reader configured to transmit power to the passive RFID transponder, and the passive RFID transponder is configured to transmit information to the RFID reader when the passive RFID transponder receives power from the RFID reader; and
   a shield, the shield having a first condition and a second condition, wherein in the first condition the shield comprises a conductive material configured to preclude at least one of the transmission of power from the RFID reader to the passive RFID transponder and the transmission of information from the passive RFID transponder to the RFID reader, in the second condition the shield is configured to permit the transmission of power from the RFID reader to the passive RFID transponder and to permit the transmission of information from the passive RFID transponder to the RFID reader, and the shield is configured to transition from the first condition to the second condition when the shield is exposed to the predetermined environmental condition; and
   wherein the interrogator indicates that the predetermined environmental condition exists when the shield transitions to its second condition, the passive RFID transponder receives power from the RFID reader and transmits the information to the RFID reader, and the RFID reader receives the information from the RFID transponder.

2. The system of claim 1, wherein the predetermined environmental condition includes a fluid proximate at least one of the device and the shield.

3. The system of claim 2, wherein the fluid includes a fluid discharged by a patient during an incontinence event.

4. The system of claim 3, wherein at least one of the device and the shield is disposed within a diaper such that the at least one of the device and the shield is positioned proximate at least one of a urine discharge orifice and a fecal discharge orifice of the patient when the diaper is worn by the patient.

5. The system of claim 2, wherein at least a portion of the shield is at least partially soluble in the fluid such that the shield at least partially transitions from the first condition to the second condition when the at least a portion of the shield at least partially dissolves when the shield is exposed to the fluid.

6. The system of claim 5, wherein the shield comprises a shielding layer and an at least partially soluble carrier, the shielding layer being at least partially disposed on the carrier, when the shield is in the first condition the shielding layer is configured to preclude the interrogator from reading information provided by the device, the at least partially soluble carrier is subject to breakdown when the carrier is exposed to the fluid, and the breakdown of the carrier at least partially transitions the shield from the first condition to the second condition.

7. The system of claim 1, wherein in the first condition the shield comprises a conductive sheet.

8. The system of claim 1, wherein in the first condition the shield comprises a conductive mesh.

9. The system of claim 1, wherein the conductive material is selected from the group consisting of conductive ink, conductive paint, and conductive grease.

10. The system of claim 1, wherein the shield comprises a facilitator configured to at least partially enable the transition of the shield from the first condition to the second condition when the shield is exposed to the predetermined environmental condition.

11. The system of claim 10, wherein the facilitator is configured to increase in volume when exposed to the predetermined environmental condition, the facilitator at least partially encloses the device, the conductive material encloses at least a portion of the device and at least a portion of the facilitator, and the increase in volume of the facilitator when it is exposed to the predetermined environmental condition induces stresses in the conductive material sufficient to at least partially rupture the conductive material.

12. The system of claim 11, wherein the conductive material includes at least one stress enhancer, the shield is configured such that the stress enhancer induces stress concentrations within the conductive material when the facilitator increases in volume, and the stress concentrations within the conductive material are sufficient to at least partially enable rupture of the conductive material.

13. The system of claim 10, wherein the shield further comprises a carrier that is subject to breakdown when the shield is exposed to the predetermined environmental condition, when the shield is in the first condition the conductive material is deposited on and supported by the carrier with the conductive material having a first surface area, the facilitator includes a non-shielding material disposed within the carrier, and the non-shielding material has a second surface area greater than the first surface area such that when the carrier breaks down upon exposure to the predetermined environmental condition the shield transitions from the first condition to the second condition as the conductive material ruptures as it becomes deposited on the non-shielding material of the facilitator.

14. The system of claim 1, wherein the information provided by the device is stored on the device.

15. A method of detecting a predetermined environmental condition, wherein the method comprises:
providing a device capable of storing information, wherein the device includes predetermined information stored thereon;
providing a non-human interrogator configured to read at least some of the information stored on the device;
providing a shield, the shield having a first condition and a second condition, wherein in the first condition the shield is configured to preclude the interrogator from reading at least some of the information stored on the device, in the second condition the shield is configured to enable the interrogator to read at least some of the information stored on the device, the shield is provided in the first condition, the shield is configured to transition from the first condition to the second condition when the shield is exposed to the predetermined environmental condition, the predetermined environmental condition includes a fluid proximate at least one of the device and the shield, and at least a portion of the shield is at least partially soluble in the fluid such that the shield at least partially transitions from the first condition to the second condition when the at least a portion of the shield at least partially dissolves when the shield is exposed to the fluid;
exposing the shield to the predetermined environmental condition such that the shield transitions from the first condition to the second condition;
reading with the interrogator the predetermined information stored on the device; and
indicating that the predetermined environmental condition exists in response to the interrogator reading the predetermined information stored on the device; and
wherein the shield comprises a shielding layer and a facilitator, when the shield is in the first condition the shielding layer is configured to preclude the interrogator from reading at least some of the information stored on the device, the facilitator is configured to at least partially enable the transition of the shield from the first condition to the second condition when the shield is exposed to the predetermined environmental condition, the facilitator is configured to increase in volume when exposed to the predetermined environmental condition, the facilitator at least partially encloses the device, the shielding layer encloses at least a portion of the device and at least a portion of the facilitator, and the increase in volume of the facilitator when it is exposed to the predetermined environmental condition induces stresses in the shielding layer sufficient to at least partially rupture the shielding layer.

16. The method of claim 15, further comprising positioning at least one of the device and the shield proximate at least one of a urine discharge orifice and a fecal discharge orifice of a patient, wherein the fluid includes a fluid discharged by the patient during an incontinence event.

17. A sensor for detecting a predetermined environmental condition, comprising:
a device capable of providing information, wherein the device includes a passive RFID transponder configured to transmit information to an external reader in response to an interrogation signal from the external reader, the interrogation signal provides operating power to the passive RFID transponder, and the device provides information in a machine-readable format; and
a shield disposed proximate the device, the shield having a first condition and a second condition, wherein in the first condition the shield comprises a conductive material configured to preclude at least one of the provision of operating power from the interrogation signal to the passive RFID transponder and the transmission of information from the passive RFID transponder to the external reader, in the second condition the shield is configured to permit the provision of operating power from the interrogation signal to the passive RFID transponder and to permit the transmission of information from the passive RFID transponder to the external reader, the shield is configured to transition from the first condition to the second condition when the shield is exposed to the predetermined environmental condition, and the sensor detects the predetermined environmental condition when the shield transitions to its second condition, the passive RFID transponder receives operating power from the interrogation signal, and the passive RFID transponder transmits the information to the external reader.

18. The sensor of claim 17, wherein in the first condition the shield comprises a conductive sheet.

19. The sensor of claim 17, wherein in the first condition the shield comprises a conductive mesh.

20. The sensor of claim 17, wherein in the first condition at least a portion of the shield is conductive ink, conductive paint, or conductive grease.

21. The sensor of claim 17, wherein the device includes first and second opposed major sides, and the shield is disposed on at least one of the first and second major sides of the device.

22. The sensor of claim 17, wherein the predetermined environmental condition includes a predetermined fluid proximate at least one of the device and the shield, and at least a portion of the shield is at least partially soluble in the predetermined fluid such that the shield at least partially transitions from the first condition to the second condition when the at least a portion of the shield at least partially dissolves when the shield is exposed to the predetermined fluid.

23. The sensor of claim 22, wherein the predetermined fluid includes a fluid discharged by a patient during an incontinence event.

24. The sensor of claim 22, wherein the shield comprises a shielding layer and an at least partially soluble carrier, the shielding layer is at least partially disposed on the carrier, when the shield is in the first condition the shielding layer is configured to prevent access to information provided by the device, the at least partially soluble carrier is subject to breakdown when the carrier is exposed to the predetermined fluid, and the breakdown of the carrier at least partially transitions the shield from the first condition to the second condition.

25. The sensor of claim 17, wherein the shield is configured to transition from the second condition to the first condition when the shield is removed from exposure to the predetermined environmental condition.

26. A sensor for detecting a predetermined environmental condition, comprising:
a device capable of providing information; and
a shield disposed proximate the device, the shield having a first condition and a second condition, wherein the shield comprises a shielding layer and a facilitator, when the shield is in the first condition the shielding layer is configured to prevent access to information provided by the device, in the second condition the shield is configured to permit access to information provided by the device, the shield is configured to transition from the first condition to the second condition when the shield is exposed to the predetermined environmental condition, the facilitator is configured to at least partially enable the transition of the shield from the first condition to the second condition when the shield is exposed to the predetermined environmental condition, the predetermined environmental condition includes the presence of a predetermined fluid proximate at least one of the device and the shield, the facilitator is configured to increase in volume when exposed to the predetermined fluid, the facilitator at least partially encloses the device, the shielding layer encloses at least a portion of the device and at least a portion of the facilitator, and the increase in volume of the facilitator when it is exposed to the predetermined fluid induces stresses in the shielding layer sufficient to at least partially rupture the shielding layer.

27. A system for detecting a predetermined environmental condition, wherein the system comprises:
a first device configured to transmit a first signal;
a second device configured to receive a second signal; and
a sensor, comprising:
a third device, wherein responsive to receipt of the first signal by the third device the third device is configured to transmit the second signal, and
a shield disposed proximate the third device, wherein the shield is configured to preclude transmission of at least one of the first signal to the third device and the second signal from the third device, and upon exposure of the shield to the predetermined environmental condition an efficacy of the shield is sufficiently disrupted such that the disrupted shield permits transmission of at least one of the first signal to the third device and the second signal from the third device; and
wherein the shield comprises a shielding layer and a non-shielding facilitator, when intact the shielding layer is configured to preclude the transmission of at least one of the first signal to the third device and the second signal from the third device, the facilitator is configured to increase in volume when exposed to the predetermined environmental condition and the facilitator at least partially encloses the third device, the shielding layer encloses at least a portion of the third device and at least a portion of the facilitator, and the increase in volume of the facilitator when it is exposed to the predetermined environmental condition induces stresses in the shielding layer sufficient to at least partially rupture the shielding layer to permit the transmission of at least one of the first signal to the third device and the second signal from the third device.

28. The system of claim 27, wherein the predetermined environmental condition includes a fluid discharged by a patient during an incontinence event.

29. A system for detecting a predetermined environmental condition, wherein the system comprises:
a first device configured to transmit a first signal;
a second device configured to receive a second signal; and
a sensor, comprising:
a third device, wherein responsive to receipt of the first signal by the third device the third device is configured to transmit the second signal, and
a shield disposed proximate the third device, wherein the shield is configured to preclude transmission of at least one of the first signal to the third device and the second signal from the third device, and upon exposure of the shield to the predetermined environmental condition an efficacy of the shield is sufficiently disrupted such that the disrupted shield permits transmission of at least one of the first signal to the third device and the second signal from the third device; and
wherein the shield comprises a shielding layer, a facilitator and a carrier that is subject to breakdown when the shield is exposed to the predetermined environmental condition, wherein when intact the shielding layer includes a conductive material that is deposited on and supported by the carrier, has a first surface area, and is configured to preclude the transmission of at least one of the first signal to the third device and the second signal from the third device, the facilitator includes a non-shielding material disposed within the carrier, and the non-shielding material has a second surface area greater than the first surface area such that when the carrier breaks down upon exposure to the predetermined environmental condition the conductive material ruptures as it becomes deposited on the non-shielding material of the facilitator which disrupts the shield and permits the transmission of at least one of the first signal to the third device and the second signal from the third device.

30. The system of claim 29, wherein the shielding layer includes a conductive material that is deposited on the carrier, wherein the conductive material is conductive ink, conductive paint, or conductive grease.

31. The system of claim 29, wherein the predetermined environmental condition includes a fluid discharged by a patient during an incontinence event.

32. A method of detecting a predetermined environmental condition, wherein the method comprises:
providing a device capable of storing information, wherein the device comprises a passive RFID transponder and includes predetermined information stored thereon, and at least some of the information stored on the device is stored on the passive RFID transponder;
providing a non-human interrogator configured to read at least some of the information stored on the device, wherein the interrogator comprises an RFID reader, the interrogator is configured to transmit power to the passive RFID transponder, and the passive RFID transponder is configured to transmit at least some of the information stored on the passive RFID transponder to the RFID reader responsive to the passive RFID transponder receiving power from the interrogator;

providing a shield, the shield having a first condition and a second condition, wherein in the first condition the shield is configured to preclude the interrogator from reading at least some of the information stored on the device by precluding at least one of the transmission of power from the interrogator to the passive RFID transponder and the transmission of at least some of the information stored on the passive RFID transponder from the passive RFID transponder to the RFID reader, in the second condition the shield is configured to enable the interrogator to read at least some of the information stored on the device by permitting the transmission of power from the interrogator to the passive RFID transponder and to permit the transmission of at least some of the information stored on the passive RFID transponder from the passive RFID transponder to the RFID reader, the shield is provided in the first condition, the shield is configured to transition from the first condition to the second condition when the shield is exposed to the predetermined environmental condition, the predetermined environmental condition includes a fluid proximate at least one of the device and the shield, and at least a portion of the shield is at least partially soluble in the fluid such that the shield at least partially transitions from the first condition to the second condition when the at least a portion of the shield at least partially dissolves when the shield is exposed to the fluid;

exposing the shield to the predetermined environmental condition such that the shield transitions from the first condition to the second condition;

reading with the interrogator the predetermined information stored on the device; and indicating that the predetermined environmental condition exists in response to the interrogator reading the predetermined information stored on the device, wherein indicating that the predetermined environmental condition exists is in response to:

the shield transitioning to its second condition, the passive RFID transponder receiving power from the interrogator, and the passive RFID transponder transmitting to the RFID reader at least some of the information stored on the passive RFID transponder.

33. The method of claim 32, further comprising positioning at least one of the device and the shield proximate at least one of a urine discharge orifice and a fecal discharge orifice of a patient, wherein the fluid includes a fluid discharged by the patient during an incontinence event.

* * * * *